(12) United States Patent
North

(10) Patent No.: US 8,386,054 B2
(45) Date of Patent: Feb. 26, 2013

(54) MODULAR ELECTRODE AND INSERTION TOOL

(76) Inventor: Richard B. North, Baltimore, MD (US)

(*) Notice: Subject to any disclaimer, the term of this patent is extended or adjusted under 35 U.S.C. 154(b) by 277 days.

(21) Appl. No.: 12/804,816

(22) Filed: Jul. 29, 2010

(65) Prior Publication Data

US 2011/0029053 A1 Feb. 3, 2011

Related U.S. Application Data

(60) Provisional application No. 61/229,774, filed on Jul. 30, 2009.

(51) Int. Cl.
*A61N 1/05* (2006.01)
(52) U.S. Cl. ......... 607/117; 607/116; 607/133; 607/149
(58) Field of Classification Search .................... 607/117
See application file for complete search history.

(56) References Cited

U.S. PATENT DOCUMENTS

| | | | |
|---|---|---|---|
| 5,000,177 A * | 3/1991 | Hoffmann et al. | 607/2 |
| 5,411,535 A | 5/1995 | Fujii et al. | |
| 6,006,124 A | 12/1999 | Fischell et al. | |
| 6,522,932 B1 | 2/2003 | Kuzma et al. | |
| 6,999,819 B2 * | 2/2006 | Swoyer et al. | 607/117 |
| 7,299,097 B2 | 11/2007 | Bardy et al. | |
| 7,383,090 B2 * | 6/2008 | O'Brien et al. | 607/116 |
| 7,792,591 B2 | 9/2010 | Rooney et al. | |
| 2002/0128700 A1 * | 9/2002 | Cross, Jr. | 607/117 |
| 2003/0171797 A1 | 9/2003 | Nova et al. | |
| 2004/0210292 A1 | 10/2004 | Bardy et al. | |
| 2005/0038489 A1 * | 2/2005 | Grill | 607/116 |
| 2006/0161235 A1 * | 7/2006 | King | 607/117 |
| 2006/0253181 A1 | 11/2006 | Schulman et al. | |
| 2007/0088335 A1 | 4/2007 | Jolly | |
| 2009/0149731 A1 | 6/2009 | Selvitelli et al. | |

FOREIGN PATENT DOCUMENTS

| | | |
|---|---|---|
| WO | 2009079704 | 7/2009 |
| WO | 2009148938 | 12/2009 |
| WO | PCT/US2010/043608 | 4/2010 |

* cited by examiner

*Primary Examiner* — Carl H Layno
*Assistant Examiner* — Michael Carey
(74) *Attorney, Agent, or Firm* — Whiteford, Taylor & Preston LLP

(57) ABSTRACT

Disclosed is a modular system for providing electrical stimulation, in which a first modular electrode section has a contoured back end configured to engage a contoured front end of another electrode section or a tool that may be used to place the first modular electrode section in the patient's body. The contours of the modular electrode section allow the two components to engage with one another so as to prevent their separation in the horizontal plane, and a lead extending from the first modular electrode is configured to engage keels on the top surface of the second electrode portion or tool, with such keels providing a snap-type attachment between the lead and the second electrode portion or tool, such that the two components may be joined together but easily separated from one another through the intentional separation of the lead from the keels on the second electrode portion or tool.

16 Claims, 5 Drawing Sheets

MODULAR ELECTRODE AND INSERTION TOOL

CROSS REFERENCE TO RELATED APPLICATION

This application is based upon and claims benefit of U.S. Provisional Patent Application Ser. No. 61/229,774 entitled "Modular Electrode and Insertion Tool", filed with the U.S. Patent and Trademark Office on Jul. 30, 2009 by the inventor herein, the specification of which is incorporated herein by reference.

FIELD OF THE INVENTION

The present invention relates generally to the field of implantable medical electronic devices, such as electrical stimulators, epidural electrodes, defibrillators and pacemakers, and more particularly to an electrode having a modular configuration allowing multiple modular electrode segments to be joined together in combination, as well as an insertion tool to aid in the surgical implantation of such modular electrode segments.

BACKGROUND OF THE INVENTION

Many humans (and other mammals and animals) receive benefit from implantable medical devices that deliver electrical pulses to or record from desired locations within their bodies. Such medical devices may comprise, for instance, spinal cord stimulation ("SCS") electrodes which typically comprise a small lead wire that is connected at one end to a power source and at the opposite end to a plurality of electrical contacts configured to transfer an electrical signal to the tissues that are to be stimulated. Those electrical contacts may, for instance, be situated in a paddle configured for implantation in a patient adjacent the tissue that is to be stimulated, such as along the spinal cord of a patient. SCS paddles typically have the lead wire or wires emerging from the bottom edge of the paddle, in the same plane as the body of the paddle. Also, typically there is a strain relief, molded along with the paddle, which surrounds the emerging lead or leads for approximately 5-8 mm, and beyond that the flexible leads continue onward to the power source.

Such paddle electrodes may be provided in a variety of configurations, with particular configurations being used for particular patient conditions. For instance, one patient's condition may require use of a single 8-electrode paddle, while another patient's condition may require use of multiple 6-electrode paddles. Thus, some instances may call for the use of multiple electrodes, wherein two or more leads are attached to a single implanted pulse generator. A common example of the use of multiple electrodes is the placement of two percutaneous SCS electrodes plugged into two corresponding ports on the implanted pulse generator. These electrodes are inserted independently into the implanted pulse generator, and while they may be anchored together subcutaneously, they are not coupled together at the ends where the stimulating contacts are located. Likewise, two or more paddle electrodes that are implanted for use with a single pulse generator are typically not coupled together.

When using multiple electrodes, a surgeon may suture two electrodes together to form a larger or longer array. In doing so, rather than performing two separate laminectomies at adjacent spinal levels to implant two electrodes, a single laminectomy may be performed to insert the two joined electrodes, using the lower electrode to push the upper electrode into position. Unfortunately, however, as the two electrodes remain separate elements not particularly configured for a modular assembly, this procedure can be quite difficult to perform.

Furthermore, while a large array of electrical contacts on a single electrode might likewise achieve the same result (i.e., providing a wider area of electrical stimulation from a single electrode assembly implanted through a single laminectomy), providing for all possibly desired large arrays would be cost-prohibitive, and likewise require the manufacture and maintenance of a stock of a large quantity of different electrodes. For instance, a large electrode, such as might be used as a thoracolumbar electrode, may be too large to use safely in the cervical spine. Similarly, insertion of a long electrode into the spine at any level may encounter an obstruction, calling for the use of a shorter electrode. Moreover, the larger array can use up contact positions on the implanted pulse generator (or recorder) which might otherwise be useful. For example, an intraspinal electrode might be supplemented by a subcutaneous electrode, with both electrodes connected to a single generator. Of course, such connection to a single generator would only be possible if there are unused contact positions available.

Still further, traditional electrodes may be quite difficult to manipulate during implantation. Presently available electrodes, with their irregular shapes and soft materials, are very difficult to grasp with standard surgical tools such as forceps, especially once they have been lubricated by body fluids in the surgical field. Often the surgical exposure is deep, narrow, and dark. Existing electrodes typically are not supplied with a specialized insertion tool, and attempting to manipulate them can be quite frustrating.

It would therefore be advantageous to provide an electrode that is configurable into varied electrical contact configurations so as to be selectively applicable to various patient conditions requiring electrical stimulation. It would also be advantageous to provide a tool suitable for aiding in the implantation and manipulation of such a variably configurable electrode.

SCS is just one example of the potential applications of the present invention; it also offers advantages for other implanted stimulator applications, including but not limited to motor cortex, peripheral nerve, subcutaneous, and sacral nerve roots. It is also applicable to recording from the same and additional locations in the body.

SUMMARY OF THE INVENTION

Disclosed is a modular system for providing electrical stimulation to a patient's body, in which a first modular electrode section has a contoured back end configured to engage with a contoured front end of another electrode section or a tool that may be used to place the first modular electrode section in the patient's body. The contours of the back end of the first modular electrode section and of the front end of the second electrode section or tool allow the two components to engage with one another so as to prevent their separation in the horizontal plane (i.e., the plane that contains the top surfaces of the two components). Additionally, in order to prohibit both the lateral and vertical separation of the two components, a lead extending from the first modular electrode is configured to engage keels on the top surface of the second electrode portion or tool, with such keels providing a snap-type attachment between the lead and the second electrode portion or tool, such that the two components may be joined together but easily separated from one another through the intentional separation of the lead from the keels on the second electrode portion or tool. With this construction, a surgeon may ensure that the two components remain connected to one another through the implantation process, and may likewise separate the components if and when desired to accommodate a particular application or clinical condition.

With regard to one aspect of a particularly preferred embodiment of the invention, a modular system for providing electrical simulation to a patient's body is provided, the modular system comprising a modular electrode section comprising an electrode body having an electrode front end, an electrode back end opposite the electrode front end, an electrode top surface, and an electrode bottom surface, the electrode back end having a contour comprising concave and convex portions, and an electrode engaging member comprising an engaging member body having an engaging member front end, an engaging member back end opposite the engaging member front end, an engaging member top surface, and an engaging member bottom surface, the engaging member front end having a contour comprising concave and convex portions that are complementary to and configured to engage with the concave and convex portions of the electrode back end.

With regard to another aspect of a particularly preferred embodiment of the invention, a modular electrode is provided comprising an electrode body having an electrode front end, an electrode back end opposite the electrode front end, an electrode top surface, and an electrode bottom surface, the electrode back end having a contour comprising concave and convex portions configured for engagement with complementary convex and concave portions on an electrode engaging member configured for attachment to the electrode body, a plurality of electrical contacts within one of the top surface and the bottom surface of the electrode body, and a plurality of wires extending from the plurality of electrical contacts to a lead configured for connection to an implantable medical device to transfer an electrical signal between the implantable medical device and the plurality of electrical contacts.

With regard to yet another aspect of a particularly preferred embodiment of the invention, an electrode engaging member configured for engaging a modular electrode is provided, the electrode engaging member comprising an engaging member body having an engaging member front end, an engaging member back end opposite the engaging member front end, an engaging member top surface, and an engaging member bottom surface, the engaging member front end having a contour comprising concave and convex portions configured for engagement with complementary convex and concave portions on a modular electrode configured for attachment to the engaging member body.

BRIEF DESCRIPTION OF THE DRAWINGS

The numerous advantages of the present invention may be better understood by those skilled in the art by reference to the accompanying drawings in which.

DETAILED DESCRIPTION OF THE INVENTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

With regard to a first aspect of a particularly preferred embodiment of the invention, a modular implantable electrode is provided, such as a SCS paddle electrode, capable of being surgically implanted inside of a patient so as to transfer an electrical signal from a power source to targeted tissue in the patient. The paddle electrode is particularly configured so as to allow multiple paddle electrode sections to be longitudinally joined together in order to allow the size of an electrical contact array to be particularly configured for a specific application or patient condition. Likewise, with regard to another aspect of a particularly preferred embodiment, an insertion tool is provided for engaging such modular paddle electrode sections to positively engage a portion of at least one of those modular sections and facilitate its handling by the surgeon.

Figure 1:
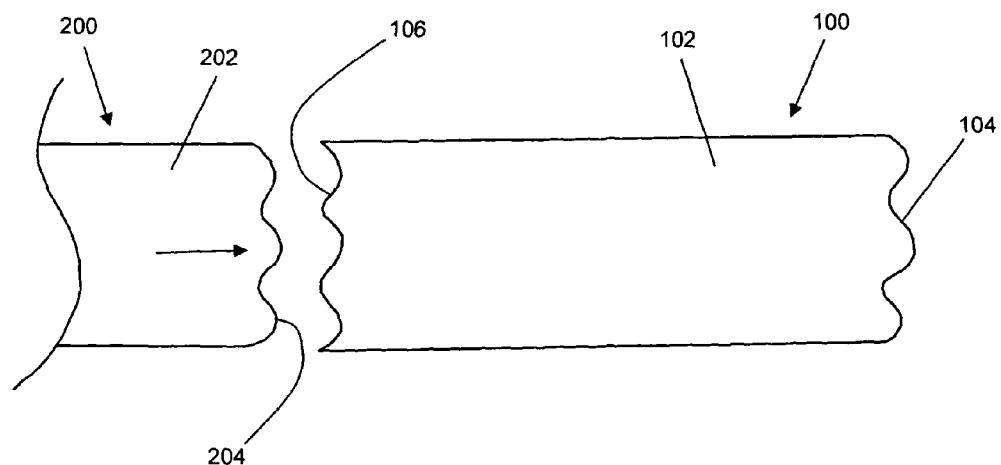
FIG. 1 is a top view of a modular electrode assembly in accordance with an aspect of a particularly preferred embodiment of the invention.

With reference to FIG. 1, a first modular paddle electrode section 100 is shown having a top surface 102, a front end 104, and a back end 106. Front end 104 is shaped with concavities and convexities that may aid in the insertion of first modular paddle electrode section 100 into the designated area within a patient. For instance, copending and co-owned U.S. patent application Ser. No. 12/804,117, filed on Jul. 14, 2010 by the inventor herein describes a shaped electrode and dissecting tool having a contoured front end configured to aid in the insertion of such electrode into a patient. The specification of patent application Ser. No. 12/804,117 is incorporated herein by reference in its entirety. Similarly, back end 106 of modular paddle electrode section 100 is shaped with complementary concavities and convexities. An electrode engaging member 200, which may comprise a second modular paddle electrode section or alternatively an insertion tool, is likewise provided, having a top surface 202, a front end 204, and a back end (not shown). Front end 204 has a contour comprised of concavities and convexities similar to the contour of front end 104 of modular paddle electrode section 100, and is configured to mate with and closely engage back end 106 of first modular paddle electrode section 100 which is itself provided with a complementary contour to the concavities and convexities of front end 204 of electrode engaging member 200. The complementary contours of back end 106 of first modular paddle electrode 100 and the front end 204 of electrode engaging member 200 allow close engagement of the two components so as to facilitate the controlled movement of first modular paddle electrode section 100 into position within the patient.

Figure 2:
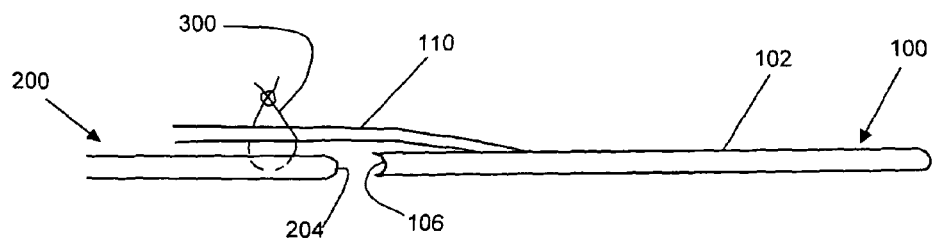
FIG. 2 is a side view of the modular electrode assembly of FIG. 1.

As shown in FIG. 2, a complementary mating configuration may also be provided in the vertical planes of back end 106 of first modular paddle electrode section 100 and front end 204 of electrode engaging member 200. More particularly, those ends may be curved so as to closely engage one another so as to resist separation in the vertical direction (as viewed in FIG. 2). While FIG. 2 particularly shows curved faces on back end 106 of first modular paddle electrode section 100 and on front end 204 of electrode engaging member 200, those of ordinary skill in the art will recognize that other mating contours, such as angled faces and edges and the like, may likewise be used to allow the two modular sections 100 and 200 to fit closely with one another, without departing from the spirit and scope of the invention.

As shown in FIG. 2, first modular paddle electrode section 100 may have a lead 110 attached thereto which is configured to transfer an electrical signal from an implanted pulse generator to electrical contacts on first modular paddle electrode section 100. As is described in co-pending and co-owned U.S. application Ser. No. 12/804,560 filed by the inventor herein on Jul. 23, 2010, titled "Electrode Having Erectable Lead," the specification of which is incorporated herein by reference in its entirety, lead 110 may emerge from the top surface 102 of modular paddle electrode section 100 so as to not interfere with the mating of back end 106 of first modular paddle electrode section 100 with front end 204 of electrode engaging member 200. Optionally, one or more sutures 300 may be used to suture emerging lead 110 to electrode engaging member 200 after its front end 204 has been mated with the back end 106 of first modular paddle electrode 100.

Figure 3:
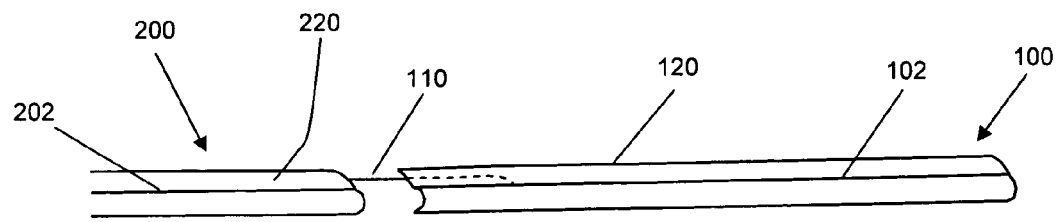
FIG. 3 is a side view of the modular electrode assembly of FIG. 1 according to another aspect of the invention.
Figure 4:
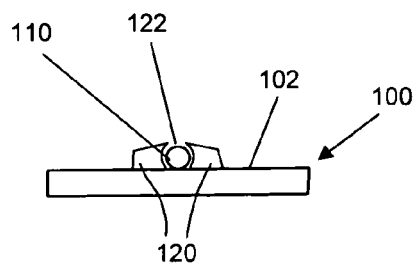
FIG. 4 is a cross-sectional view of the modular electrode assembly of FIG. 3.

Alternatively, and as shown in FIGS. 3 and 4, first modular paddle electrode section 100 may be provided keels 120 on its top surface 102. Keels 120 are formed so as to provide a channel which closely receives lead 110, such that after lead 110 is snapped into place, keels 120 hold lead 110 in place absent the application of a significant force to withdraw it from the keels. For instance, keels 120 may have concave surfaces on their interiors which closely follow the outer dimension of lead 110. A slit 122 is provided between keels 120 through which lead 110 may be inserted. Keels 220 on electrode engaging member 200 are similarly configured, again having a slit through which lead 110 may be inserted, thus helping to hold electrode engaging member 200 to first modular paddle electrode section 100 after their respective front end 204 and back end 106 are mated with one another.

Figure 5:
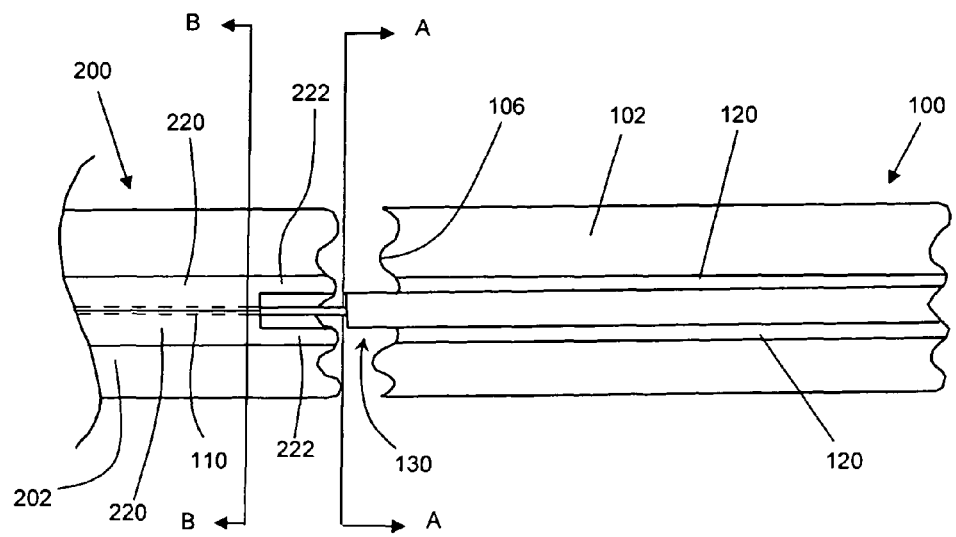
FIG. 5 is a top view of a modular electrode assembly according to another aspect of the invention.
Figure 6:
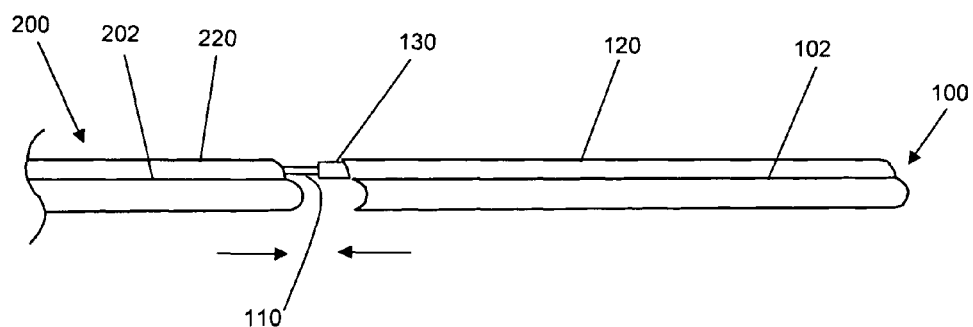
FIG. 6 is a side view of the modular electrode assembly of FIG. 5.

With regard to another aspect of the invention, and as shown in FIGS. 5 and 6, a strain relief 130 is provided around lead 110, which strain relief 130 extends outward beyond back end 106 of first modular paddle electrode section 100. Electrode engaging member 200 is again provided keels 220, again having a slit at the top surface between the two keels 220 capable of receiving lead 110. The front most portions of keels 220 are of similar configuration to keels 120 on first modular paddle electrode section 100, comprising two thin walls 222 configured to receive and hold strain relief 130 when the two modular paddle electrode sections 100 and 200 are mated with one another. As best seen in FIG. 5, walls 222 at their back ends open into a wider portion of keels 220, with keels 220 having such wider thickness throughout the rest of their length along the top surface 202 of electrode engaging member 200, with a slit (as mentioned above) configured to receive and hold lead 110. As keels 220 are thus configured to receive both lead 110 and the back-most portion of strain relief 130, once the first modular paddle electrode 100 is mated with electrode engaging member 200, and strain relief 130 and lead 110 are snapped between the appropriate sections of keels 220, the two sections 100 and 200 will likewise be held to one another by such connection.

Figure 7:
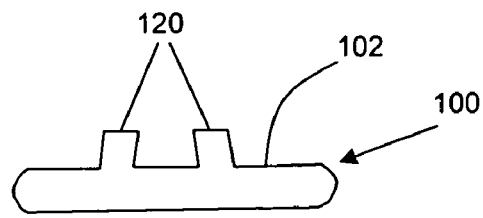
FIG. 7 is a cross-sectional view of a portion of the modular electrode assembly of FIG. 5.

As shown in the cross-sectional view of FIG. 7 (showing first modular paddle electrode section 100 without strain relief 130 installed), keels 120 extend upward from top surface 102 and at an angle less than ninety degrees to top surface 120, thus leaning toward one another to form a trapezoidal opening between them. Strain relief 130 is preferably provided a complementary trapezoidal external configuration, such that strain relief 130 may be snapped into the opening formed between keels 120. Those of ordinary skill in the art will appreciate that shapes other than a trapezoidal configuration, such as curved or angled cross-sections that are configured to removably hold strain relief 130 to first modular paddle electrode 100, may likewise be implemented without departing from the spirit and scope of the invention.

Figure 8:
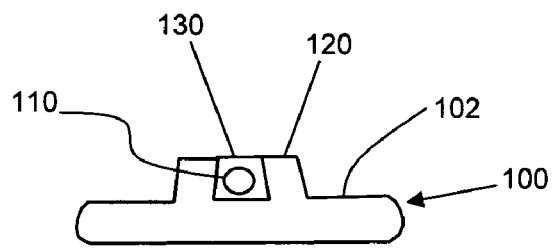
FIG. 8 is a cross-sectional view of the modular electrode assembly of FIG. 5 along section line A-A.
Figure 9:
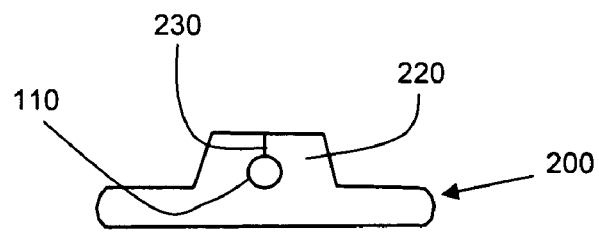
FIG. 9 is a cross-sectional view of the modular electronic assembly of FIG. 5 along section line B-B.

As shown in the cross-sectional view of FIG. 8 taken along section line A-A of FIG. 5, strain relief 130 is shown positioned between keels 120, with lead 110 extending outward from strain relief 130. Likewise, as shown in the cross-sectional view of FIG. 9 taken along section line B-B of FIG. 5, lead 110 is shown positioned within the opening between keels 220, with a narrow slit 230 positioned at the top between the top portions of keels 220, through which lead 110 may be inserted. In the case where electrode engaging member 200 is configured as a second electrode section that is to be mated with first modular paddle electrode section 100, electrode engaging member 200 may be formed from a soft silicone elastomer material, in which case slit 230 may be very narrow. In the event that electrode engaging member 200 is configured as an insertion tool that is to be mated with first modular paddle electrode section 100, a hard plastic would likely comprise such insertion tool, in which case a wider slit 230 would be desirable. Lead 110 typically comprises a plurality of wires encased within a plastic sheath which is somewhat compressible, such that it may snap into a slot in either of the foregoing configurations.

Figure 10:
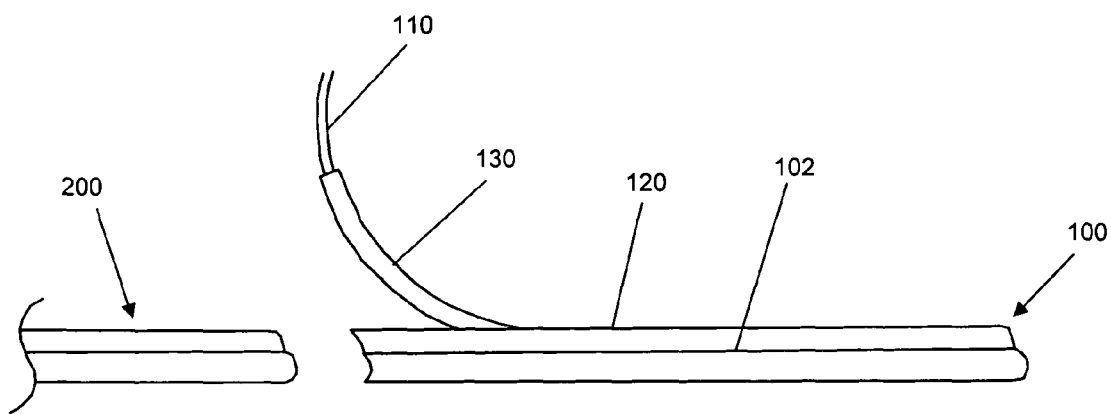
FIG. 10 is a side view of the modular electronic assembly of FIG. 5 according to another aspect of the invention.

Still further, as shown in the side view of FIG. 10, and with regard to another aspect of the invention, strain relief 130 and lead 110 may be pulled up and out of first modular paddle electrode section 100 over a portion of its length in order to facilitate assembly with electrode engaging member 200.

Those of ordinary skill in the art will recognize that by providing electrode engaging member 200 with a front end 204 configured to mate with the back end 106 of first modular paddle electrode section 100, and by providing such components with mating keels and slots as described above to engage one another, the combined features of the contoured ends of each component, the strain relief 130 and lead 110 and keels 120 and 220 will offer a much better grip to hold the two components together than has been previously achieved.

It should be understood that various other characteristics of the novel modular electrode of the current invention may be changed without departing from the spirit and scope of the present invention. For instance, additional features may be provided to further supplement the connection between the two components, such as a sleeve around the joint (which sleeve could be removable during or after insertion), or additional tabs, stiffening wires, or the like with corresponding receptacles in first modular paddle electrode section 100. Likewise, additional connections may be provided between first modular paddle electrode section 100 and electrode engaging member 200 to further supplement their connection. Still further, the foregoing configurations could likewise be used to join electrodes not only end to end, as described herein, but likewise side by side, or otherwise as may be apparent to those of ordinary skill in the art.

It is believed that the present invention and many of its attendant advantages will be understood by the forgoing description. It is also believed that it will be apparent that various changes may be made in the form, construction and arrangement of the components thereof without departing from the spirit and scope of the invention or without sacrificing all of its material advantages. The form herein before described is merely an explanatory embodiment thereof.

I claim:

1. A modular system for providing electrical stimulation to a patient's body, comprising:
   a first implantable modular paddle electrode section comprising a first electrode body having a first electrode front end, a first electrode back end opposite said first electrode front end, a first electrode top surface, and a first electrode bottom surface, said first electrode back end having a contour comprising concave and convex portions, and a lead extending from said first implantable modular paddle electrode configured for connection to an implantable medical device to transfer an electrical signal between said implantable medical device and said plurality of electrical contacts; and
   a second implantable modular paddle electrode section comprising a second electrode body having a second electrode front end, a second electrode back end opposite said second electrode front end, a second electrode top surface, and a second electrode bottom surface, said second electrode front end having a contour comprising concave and convex portions that are complementary to the concave and convex portions of said first electrode back end, and are configured to, from an initially disengaged configuration, removably engage with the concave and convex portions of said first electrode back end so that said first implantable modular electrode section becomes detachably connected to said second implantable modular electrode section, and so that advancing said second implantable modular electrode section through a patient's body will cause advancement of said first implantable modular electrode through said patient's body, said second implantable modular paddle electrode further comprising a lead-receiving channel configured to removably hold said lead extending from said first implantable modular paddle electrode so as to prevent unintentional separation of said first implantable modular paddle electrode from said second implantable modular paddle electrode, and configured to allow disengagement of said lead extending from said first implantable modular paddle electrode.

2. The system of claim 1, further comprising a plurality of electrical contacts within one of said top surface and said bottom surface of said first modular paddle electrode section, and a plurality of wires extending from said plurality of electrical contacts to said lead.

3. The system of claim 2, wherein said second modular paddle electrode section further comprises a second plurality of electrical contacts within one of said top surface and said bottom surface of said second implantable modular electrode section, and a plurality of wires extending from said plurality of electrical contacts to a second lead configured for connection to an implantable medical device to transfer an electrical signal between said implantable medical device and said second plurality of electrical contacts.

4. The system of claim 1, wherein said lead extends upward and away from said first electrode body at a point between said first electrode front end and said first electrode back end.

5. The system of claim 1, wherein said lead-receiving channel further comprises facing keels positioned on said second electrode top surface, wherein facing sides of said keels comprise convex walls, wherein said lead is positioned between said keels, and wherein at least a portion of said lead is removable from between said keels.

6. The system of claim 1, said lead further comprising a strain relief portion that extends from a point on said electrode body toward and beyond said first electrode back end, and a lead cable portion of smaller diameter than said strain relief portion and extending outward from said strain relief portion.

7. The system of claim 6, said lead-receiving channel further comprising facing keels positioned on said second electrode top surface, said keels having a first portion extending from said second electrode front end to an intermediate point on said second electrode top surface, and a second portion extending from said intermediate point toward said second electrode back end, and wherein said first portion of said keels define a first gap there between having a first gap thickness, and wherein said second portion of said keels define a second gap there between having a second gap thickness that is smaller than said first gap thickness.

8. The system of claim 7, wherein said strain relief portion is configured to fit between and remain removably attached to said first portion of said keels, and said lead cable portion is configured to fit between and remain removably attached to said second portion of said keels.

9. A modular electrode comprising:
   a first implantable modular paddle electrode having a first electrode front end, a first electrode back end opposite said first electrode front end, a first electrode top surface, and a first electrode bottom surface, each of said first electrode front end and said first electrode back end having a contour comprising concave and convex portions configured for removable engagement with and detachable connection to complementary convex and concave portions on a second implantable electrode, said first implantable electrode further comprising a plurality of electrical contacts within one of said first electrode top surface and said first electrode bottom surface, and a plurality of wires extending from said plurality of electrical contacts to a first lead configured for connection to an implantable medical device to transfer an electrical signal between said implantable medical device and said plurality of electrical contacts; and
   a lead-receiving channel configured to removably receive and hold a second lead extending from a second implantable modular paddle electrode so as to prevent unintentional separation of said first implantable modular paddle electrode from said second implantable modular paddle electrode, and configured to allow disengagement of said second lead.

10. The modular electrode of claim 9, wherein said first lead extends from said first implantable modular electrode outward from said first electrode back end.

11. The modular electrode of claim 10, wherein said first lead extends upward and away from said first implantable modular electrode at a point between said first electrode front end and said first electrode back end.

12. The modular electrode of claim 10, wherein said lead-receiving channel further comprises facing keels positioned on said first implantable modular electrode top surface, wherein facing sides of said keels comprise convex walls, wherein said keels are configured to removably receive said second lead between them, and wherein at least a portion of said second lead is removable from between said keels.

13. The modular electrode of claim 10, said first lead further comprising a strain relief portion that extends from a point on said first implantable modular electrode toward and beyond said electrode back end, and a lead cable portion of smaller diameter than said strain relief portion and extending outward from said strain relief portion.

14. A method for implanting an implantable medical device comprising:

providing an implantable modular paddle electrode comprising a first implantable modular paddle electrode section and a second implantable modular paddle electrode section configured for detachable connection to said first implantable modular paddle electrode section, said second implantable modular paddle electrode section further comprising a lead-receiving channel configured to removably hold a lead extending from said first implantable modular paddle electrode section so as to prevent unintentional separation of said first implantable modular paddle electrode section from said second implantable modular paddle electrode section, and configured to allow disengagement of said lead;

detachably connecting said lead extending from said first implantable modular electrode section to said second implantable modular electrode section; and implanting said assembled implantable modular paddle electrode at a target location within a patient's body.

15. The method of claim 14, wherein said assembling step comprises matching an electrode back end on said first implantable modular electrode section with an electrode front end on said second implantable modular electrode section that is configured to detachably connect to said electrode back end.

16. The method of claim 15, wherein said assembling step further comprises securing said lead from said first implantable modular electrode section to said second implantable modular electrode section.

* * * * *